(12) United States Patent
Weiland et al.

(10) Patent No.: US 6,424,414 B1
(45) Date of Patent: Jul. 23, 2002

(54) METHOD AND APPARATUS FOR DETECTING REFRACTIVE DEFECTS IN TRANSPARENT CONTAINERS

(75) Inventors: Joseph G. Weiland, Valencia; Edward J. Fisher, South Park, both of PA (US)

(73) Assignee: AGR International, Inc., Butler, PA (US)

( * ) Notice: Subject to any disclaimer, the term of this patent is extended or adjusted under 35 U.S.C. 154(b) by 30 days.

(21) Appl. No.: 09/690,112

(22) Filed: Oct. 16, 2000

(51) Int. Cl.$^7$ .............................................. C01N 21/90
(52) U.S. Cl. ................. 356/239.4; 250/223 B
(58) Field of Search .......................... 356/239.1, 239.4, 356/428; 250/223 B (56) References Cited

U.S. PATENT DOCUMENTS

| | | | |
|---|---|---|---|
| 4,487,322 A | | 12/1984 | Juvinall |
| 4,601,395 A | * | 7/1986 | Juvinall et al. ............. 356/428 |
| 4,610,542 A | * | 9/1986 | Ringlien .................. 356/239.4 |
| 4,924,083 A | | 5/1990 | Ishikawa et al. |
| 5,004,909 A | * | 4/1991 | Fukuchi ................... 356/239.4 |
| 5,216,481 A | * | 6/1993 | Minato .................... 356/239.1 |
| 6,304,323 B1 | * | 10/2001 | Ishikura et al. ........... 356/239.4 |

* cited by examiner

Primary Examiner—Richard A. Rosenberger
(74) Attorney, Agent, or Firm—Arnold B. Silverman; Eckert Seamans Cherin & Mellott, LLC (57) ABSTRACT

A method of inspecting a transparent container for refractive defects includes positioning a light source in spaced relationship with respect to a detector which is operatively associated with a processor for receiving electrical signals from the detectors responsive to light passing through the container being received by the detector. The method includes positioning a grid filter having a plurality of alternating dark and light bands adjacent the light source so as to provide a multiple intensity gradient to the container. The container is positioned between the light source and the detector with the grid filter serving to provide adjacent alternate light and dark bands of light impinging on the container. Refractive defects will cause a distortion of the intensity gradient which will be received by the detector. In a preferred embodiment, a plurality of light and dark bands are generally horizontally oriented and produces a generally triangular wave having a constant absolute slope. A processor is employed to receive the electrical signals emitted by the detector responsive to the light impinging thereon and make a determination as to whether refractive defects exist while ignoring desired irregularities in the container. Corresponding apparatus which employs alternating light and dark bands in the grid filter and in the preferred embodiment employs dark bands of single intensity gradient and light bands of single intensity gradient. Each band has a constant gradient of light intensity passing therethrough. The grid filters produces a triangular wave having a constant absolute slope.

51 Claims, 6 Drawing Sheets

METHOD AND APPARATUS FOR DETECTING REFRACTIVE DEFECTS IN TRANSPARENT CONTAINERS

BACKGROUND OF THE INVENTION

1. Field of the Invention

The present invention provides a method for inspecting transparent containers for refractive defects and associated apparatus. More specifically, the invention provide:s for a multiple intensity gradient light grid filter which converts light emitted by a diffuse light beam into a light gradient which impinges upon a transparent container with a detector receiving light passing through the container and emitting responsive electrical signals to a processor which determines whether a refractive defect exists in the container.

2. Description of the Prior Art

It has long been known to inspect various properties of transparent containers by passing a light beam through the container and having detectors receive the light passing therethrough, convert the light into corresponding electrical signals and deliver the signal to a suitably programmed processor which compares the received signal with a stored standard in order to determine a given characteristic of the container.

U.S. Pat. No. 4,924,083 discloses a method and apparatus for inspecting a sidewall of a bottle wherein a moving slit is synchronized with the detection means to introduce a gradient in the light source to enhance the view of refractive defects. The nature of this system, however, imposes a meaningful limitation on speed of inspection, enhances only horizontal edges of the container and provides a system which would require substantial maintenance.

U.S. Pat. No. 4,610,542 discloses a system wherein a single linear lamp is positioned behind and at the top of the diffuser. This causes the diffuser to emit more light in the upper portion than at the bottom with a smooth gradient from light to dark in between. A lens positioned near the diffuser collimates the light in order that different intensities are projected in different directions with a smooth gradation from top to bottom. This system is disclosed as only viewing the front wall of the container. This system is designed to be insensitive to small cosmetic type defects and large gentle thickness variations such as settle waves which may occur on the inside of the container wall, for example.

U.S. Pat. Nos. 4,487,322 and 4,601,395 disclose placing a filter over a diffuse light source which backlights the container to provide a single intensity gradient of light to dark parallel to the container's longitudinal axis. A lens is said to focus the light from a narrow vertical area on the front surface of the container onto a plurality of sensors arranged in the vertical column. The recorded intensity of the adjacent detectors is then compared with a bottle which passes inspection. The variation would be equal from detector to detector. This system, however, examines only the front wall of the container. It also requires that the container be axially rotated in order to inspect 360° of the sidewall. Such rotation limits inspection speed as well as requiring additional maintenance. The system is intended primarily to detect horizontally oriented transparent defects, such as ribbon tears, for example. These are large horizontal defects that are structurally hazardous.

U.S. Pat. No. 4,601,395 also discloses a filter composed of transversely spaced outer zones of substantially uniform illumination intensity and a third central zone between first and second zones in which the intensity of the diffused illumination is different from the intensities of the outer zones. These systems are designed primarily to enhance gross defects such as ribbon tears and the like which compromise the strength of the container, but are not designed to also detect cosmetic defects in the container.

U.S. Pat. No. 5,004,909 discloses alternating in black and white stripes in a diffuse light source to enhance the view of refractive defects. The containers must be rotated in order to achieve inspection of the full sidewall. A simple comparison of light levels on three adjacent sensing elements is employed to detect the refractive index. The gradient produced by the solid black to solid white stripes results in a complex image as it enhances the normal non-defect thickness variations in addition to refractive defects. As a result, it lacks the capability of efficient sorting between defects and non-defects in normal container production.

U.S. Pat. No. 5,216,481 discloses alternating black and white stripes of diffuse light source to enhance the view of refractive defects. A two-dimensional detecting means is employed and multiple inspection zones are provided to establish circumferential inspection coverage.

In spite of the foregoing disclosures, there is lacking an effective method and associated apparatus for effecting efficient inspection of transparent containers such that refractive defects including minor defects can be detected in an automated, rapid, accurate fashion while avoiding rejections based upon purposeful features, such as detection of desired regions which lack wall uniformity.

SUMMARY OF THE INVENTION

The present invention has met the hereinbefore-described needs.

The method of the present invention includes inspection of a transparent container, such as a glass container, for refractive defects by positioning the container between a light source and a detector, passing diffused light from the light source through a grid filter which establishes multiple intensity gradient bands which impinge on and inspect both the front and rear container walls for refractive defects which may be structural in nature or cosmetic in nature. The grid filtered multiple intensity gradient light passes through the container walls and is received by a detector which converts the light received into responsive electrical signals which are delivered to a processor which determines whether a refractive defect exists.

The method of the present invention does not require axial rotation of the container and preferably has the light and dark bands of the grid filter being alternated with each having light transmission properties of about 1 to 80%. The processor also avoids rejection of the container based upon desired or purposeful irregularities in the container wall.

The apparatus of the present invention provides a diffuse light source, a grid filter which preferably has a plurality of alternating light and dark bands which provide intensity gradients throughout the field of view with a lens directing the grid filtered light through the transparent container wall of the container being inspected. The light passing through container walls which do not have a refractive defect either of a structural or objectionable cosmetic variety will provide predetermined light impinging on the detector which in turn converts the light into corresponding electrical signals. The processor which may be any suitably programmed computer having stored information regarding the nature of defects which will result in rejection of the container, and preferably the irregularities in the container wall which are deemed acceptable, will effect a comparison between the electrical signals and the information and make a determination as to whether the container is rejected.

It is an object of the present invention to provide a method and associated apparatus for efficiently and rapidly inspecting transparent containers for refractive defects.

It is a further object of the present invention to provide such a method and apparatus which will not only determine the presence of refractive defects which provide a structural problem, but also those which provide a meaningful cosmetic problem.

It is a further object of the present invention to provide such a system which will, in processing information, distinguish between refractive defects and desired irregularities in a portion of a container wall.

It is yet another object of the present invention to provide such an inspection system which will effect inspection without requiring axial container rotation.

It is a further object of the present invention to provide such a system which makes shallow defects visible, while permitting inspection of a large field of view.

It is yet another object of the present invention to provide such a system which inspects both the front wall and rear wall of a container at substantially the same time.

It is another object of the present invention to provide such a system which employs a triangular wave having a constant absolute slope.

It is yet another object of the present invention to provide a system for determining the presence of horizontal and oblique cosmetic refractive defects which are of a subtle nature.

These and other objects of the invention will be more fully understood from the following detailed description of the invention on reference of the illustrations appended hereto.

DISCLOSURE OF THE PREFERRED EMBODIMENTS

As employed herein, the term "refractive defect" means a defect in a transparent container wall which includes a defect of a predetermined magnitude resulting from either (a) a variation in the thickness of the container wall in a particular region or (b) a variation in refractive index in a particular portion of the container wall and shall expressly exclude desired irregularities, such as mold seams, support rings, finishes, lettering, decorative or informational irregularities, and desired thickness changes.

Figure 1:
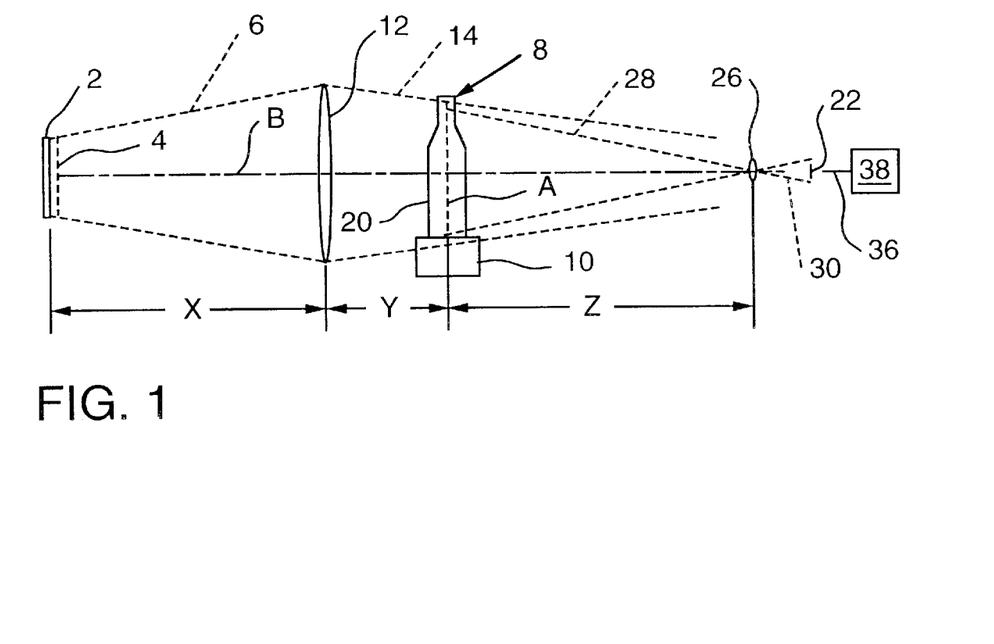
FIG. 1 is a schematic illustration of a form of inspection apparatus of the present invention.

Referring now in greater detail to FIG. 1, there is shown a light source 2 which is structured to emit diffused light which passes through grid filter 4. A glass container 8 to be inspected is positioned at a container inspection station 10 which may be a continuous conveyor, a stationary support, or any other suitable structure. In order to enhance the efficiency of light transmission of the multiple intensity gradient beam 6 emerging from the grid filter 4, the diverging light beam 6 is converted by lens 12 into converging light beam 14 which impinges upon the container wall 20. In general, the container 8 may be inspected from a position just below the finish or support ring down to the top of the base. In the form shown, the distance X, between the diffused light source 2 and the output of lens 12, may, be, for example, about 14 inches, and the distance Y, between the output surface of lens 12 and the longitudinal axis A of the transparent container 8, may be, for example, about 4 to 12 inches. A detector 22 receives the light passing through transparent glass container 8. The spacing Z between the central longitudinal axis A of the container 8 and lens 26 which focuses converging light beam 28 on detector 22 by creating diverging light beam 30 may be, for example, about 20 to 25 inches. The light source 2 is aligned with detector 22 along a longitudinal axis B. The detector 22, which may be any suitable means for converting received light to a responsive output electrical signal which is delivered by line 36 to processor 38 may, for example, be a ccd camera or a cmos detector array. If the former, it may, for example, have about 620×484 pixels. The processor 38 may be any suitably-programmed computer which contains stored information regarding what shall be deemed to be a refractive defect, either structural or cosmetic. It preferably also contains information that will cause the system not to reject on the basis of purposeful irregularities in the container wall.

The light is directed toward the container and imaged nominally about 10 to 100 inches behind the detector 22. This assures that the grid lines will not be compressed by normal container wall curvatures, thereby eliminating a possible undesired reading of a defect which does not exist. The detector 22 is focused on a container axis and has sufficient depth of the field to acquire a sharp image of both the front and back surfaces of both the front and back container walls.

Figure 2:
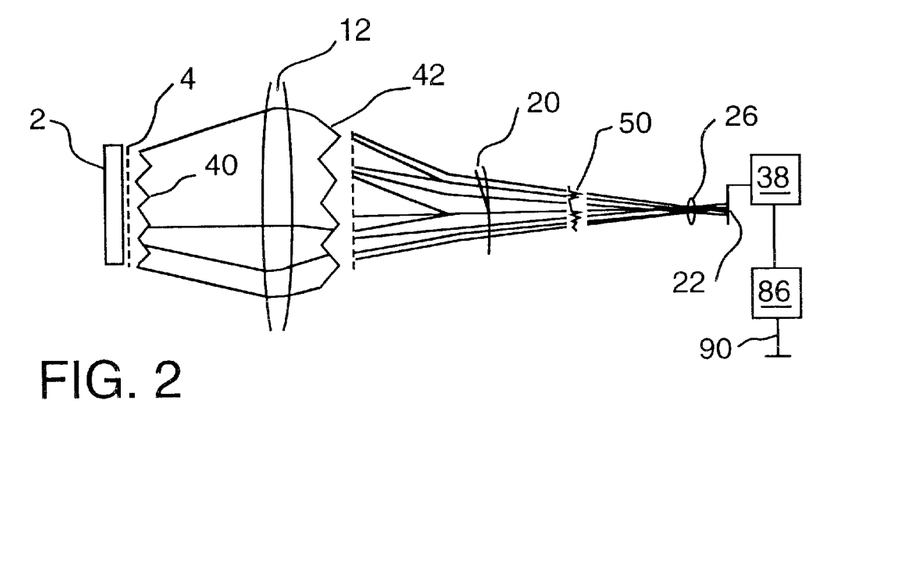
FIG. 2 is a schematic illustration showing examples of paths of light rays moving from the light source to the detector.
Figure 3:
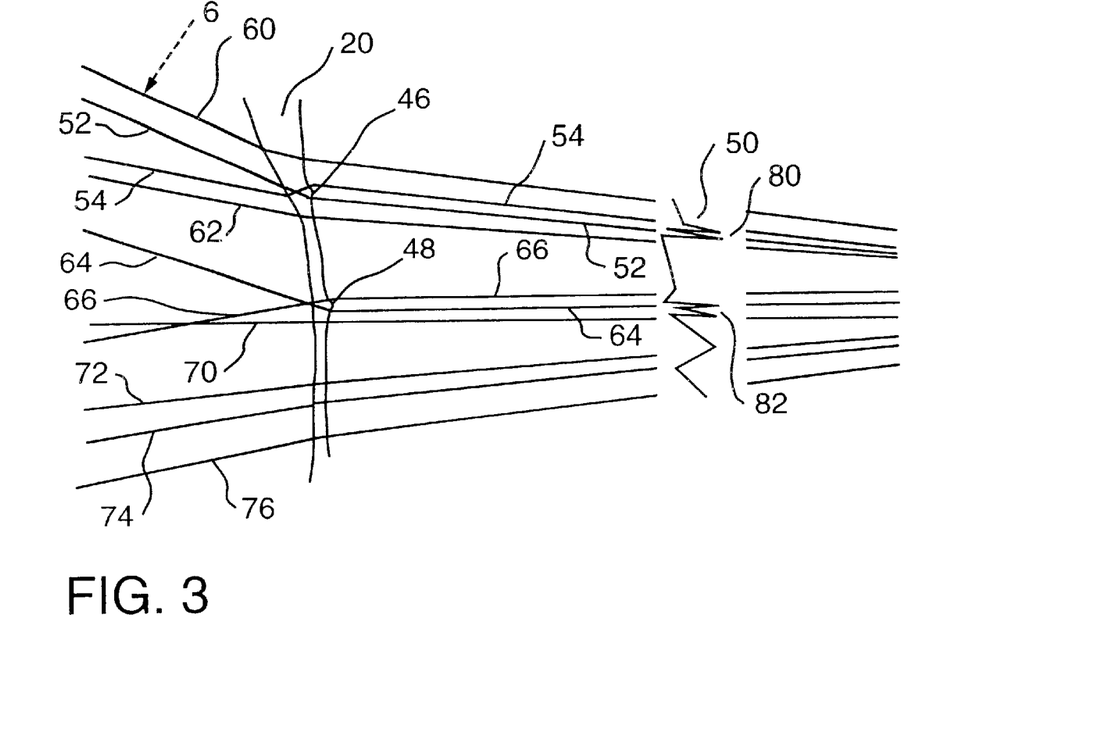
FIG. 3 is an enlarged schematic view showing a portion of the light rays of FIG. 2.

Referring in greater detail to FIGS. 2 and 3, the light beams will be considered more specifically. Light rays 60, 62, 70, 72, 74, and 76 are normal light rays refracted slightly due to slight bottle thickness variations. Rays 52, 54, 64, 66 are rays bent strongly by refractive defects 46, 48 in bottle wall 20. These bends are greatly exaggerated for clarity of illustration. While the rays will be continuous through the right-hand portion of FIG. 3, a gap has been provided to more clearly represent the large gradients 80, 82. The ten rays to the right of FIG. 3 are a continuation of the rays to the left. The three different cross-sectional profiles in FIG. 2 and the one in FIG. 3 show how the gradients change from constant slopes before the wave front goes through the container wall 20 to the distorted one after passage through the defects. This distorted pattern results in higher gradients (the sharper peaks) which the computer sees as a defect.

Figure 4A:
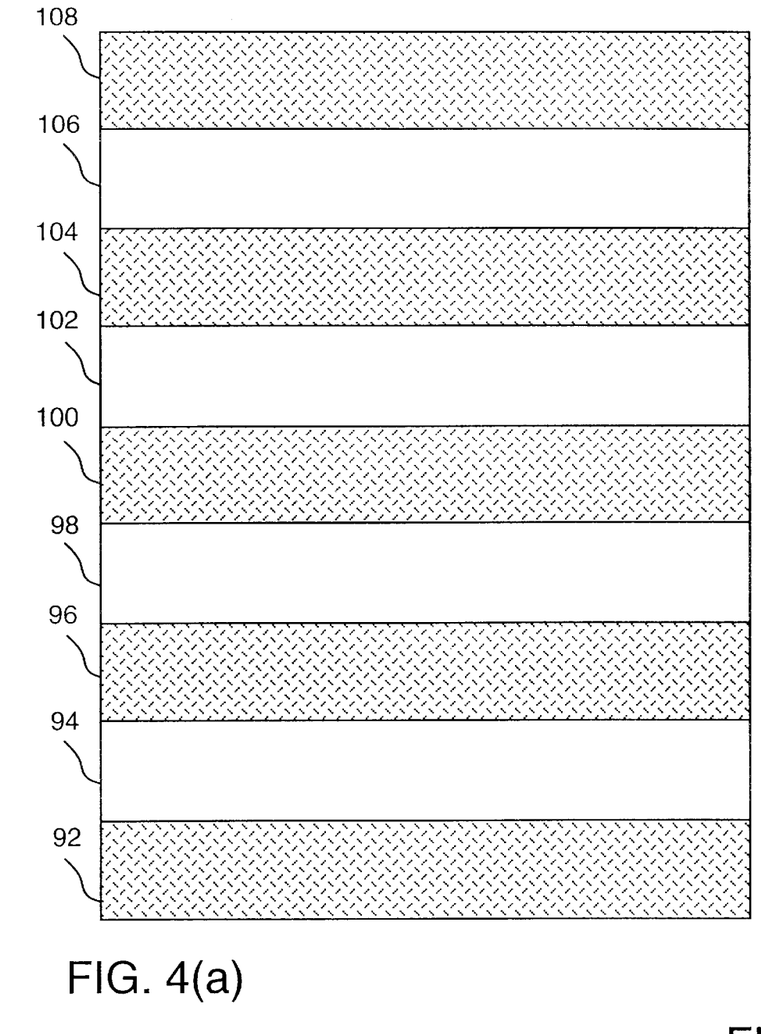
FIG. 4(a) is an image of the grid filter overlying and FIG. 4(b) is a cross-sectional profile of the transmission across the filter of FIG. 4(a).
Figure 4B:
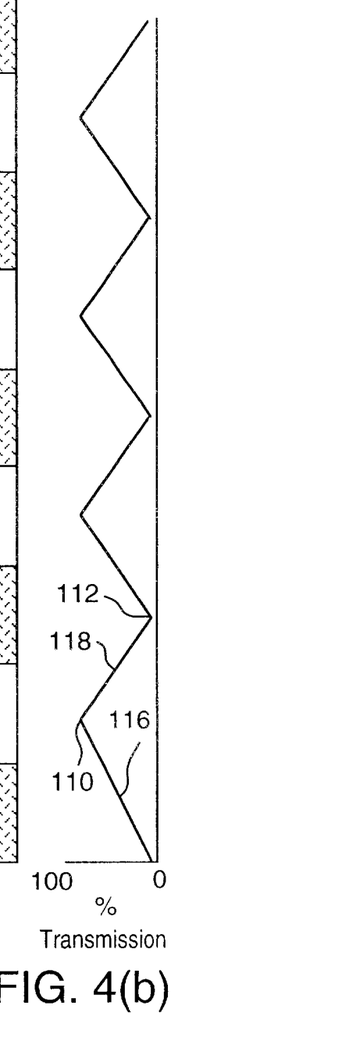

A form of grid filter of the present invention, as shown in FIGS. 4(a) and 4(b), will be described in greater detail hereinafter. The grid filter has alternating dark and light bands so as to create a sawtooth light gradient. This gradient is a uniform steep gradient of light intensity over the entire region of interest or field of view. The region of interest or field of view is then analyzed within a processor with a digital filter that will identify any gradients in the digital image that substantially exceeds the gradient in the digital filter. As will be described in greater detail herein, the digital filter seeks steep gradients (sharp edges) that are indicative of grid lines that have been refracted through refractive defects. This gradient, as it emerges from the grid filter 4, is shown at reference number 40 in FIG. 2 and, after passage through lens 12, is shown as sawtooth representation 42. The glass container wall is shown m FIGS. 2 and 3 as 20 and, in the form shown, has a pair of refractive defects 46, 48 in wall 20. The effect of the defects on light beam 6 and its component elements is shown by the changes in wavefront profile 50 resulting from the crossing of beam component 52 with beam component 54 as they pass through defect 46 while other beam components, such as 60 and 62, for example, pass through without such a crossover. Similarly, beams 64, 66 crossover as they pass through defect 48 while beam components 70, 72, 74, 76 do not. The changes in the waveform are shown by the large gradients at 80, 82 in the sawtooth pattern 50 emerging from the container. These large gradients 80, 82 refer to sharp peaks in cross-section. These peaks have very steep sides which represent sharp transitions from dark and light or light to dark on the image. Such large gradients are caused by refractive effects of the refractive defect on the light rays.

It will be appreciated that, in the absence of a defect, the detector 22 will emit electrical signals responsive to and corresponding to the impinging light to the processor 38 which, in turn, will through comparison, determine that no objectionable refractive defects, either structural or cosmetic, exist. On the other hand, when defects, such as 46 and 48 exist, the detector 22 receives a different light pattern and emits the responsive electrical signals to processor 38 which will determine that a defect exists and emit a reject signal to reject mechanism 86 (FIG. 2) which has a reject arm 90 adapted to remove a defective container from a conveyor or inspection station in a manner well known to those skilled in the art.

Referring still to FIGS. 4(*a*) and 4(*b*), in order to provide a steep gradient that will make shallow refractive defects visible while still covering a large field of view, the sign of the gradient is reversed periodically while traversing the field of view. This is represented by the sawtooth configuration of FIG. 4(*b*).

Referring now in greater detail to FIGS. 4(*a*) and 4(*b*), there is shown a grid filter 4 of the present invention which has alternating horizontal light and dark bands, such as 92, 94, 96, 98, 100, 102, 104, 106, for example. These are preferably horizontally oriented so as to provide a multiple intensity gradient of light which impinges on the container 8. In the preferred embodiment, dark bands 92, 96, 100, 104, 108 will have a minimum transmission rate of about 0.1% to 5% and will alternate with single light bands 94, 98, 102, 106, which will have a maximum transmission rate of about 70% to 100% with the alternating light and dark bands preferably having a single absolute value for the gradient in the grid filter 4. The term "absolute value" is in the mathematical sense, meaning take the value irrespective of the positive or negative sign which in this case means positive or negative slope. As shown in the adjacent graph in FIG. 4(*b*), it is preferred that the width of the light bands 94, 98, 102, 106 is generally equal to the width of the dark bands 92, 96, 100, 104, 108. The bands preferably have a light transmission of about 1% to about 80%. In order to facilitate detection of small, refractive defects of a cosmetic nature without enhancing gradual thickness changes in the container, it is preferred that the gradient bands have a frequency of about 0.25 to 3 gradient bands per inch measured across the gradient.

As shown in FIG. 4*b*, the variation and intensity of the light passing through the grid filter will be considered. It is noted that the maximum light transmission through the filter will occur at 110 which is generally midway between the lateral edges of light band 94 and the minimum light transmission 112 will occur generally midway between the lateral edges of dark band 96. It is also noted that the slope of the plot in going from the origin of the plot to maximum 110 along slope 116 has a positive sign, whereas the slope of the line 118 going between maximum 110 and minimum 112 has a negative sign. The important feature is not so much the change in sign of the slope, but the slope or rate of change.

The filter 4 in principle has a transmission of light that can vary from 0% dark, or opaque, to 100%, which is clear. For purposes of the present invention, the contrast that 0% to 100% gives is not desired. That range is too strong. In the preferred embodiment, the present invention lets about 1% of the light through in the dark bands of the triangular wave and about 80% through in the light band peaks. How fast that change happens as one moves across the triangular waves is the "gradient." If it changes quickly, the gradient is "steep" as in when one goes up a steep hill, the altitude changes very fast for a given horizontal distance. In the invention, the image processing software in the computer or processor 38 is looking for gradients that are above a certain grid slope. If we give the grid filter a constant absolute gradient or slope, the software will not see it if it is below a set gradient. The steeper the slope, the more sensitive the software is to transparent defects. If one wants a field of view that covers 8 inches, for example, there is a limit to the slope as one progresses from 100% light to 0% opaque. The present invention is unique in having the light vary from light to dark at a constant rate, but keeps changing direction of the slope. The computer is not influenced by what direction the slope is (up or down), as it only measures the gradient. The prior art used multiple solid bars which alternated clear (100%) or opaque (0%) or used a single gradient (one, even constant slope), or used a sine wave profile which is not a constant slope. The present system uses a grid which is a triangular wave which is always a constant slope. When the wave front encounters a refractive defect, the defect bends or compresses the image of the triangular wave in that area and makes the slope steeper. This is then detected as a defect by the computer software.

It will be appreciated that the intensity of the light passing through the grid filter will change constantly as a result of the constant slope or constant gradient.

Figure 5:
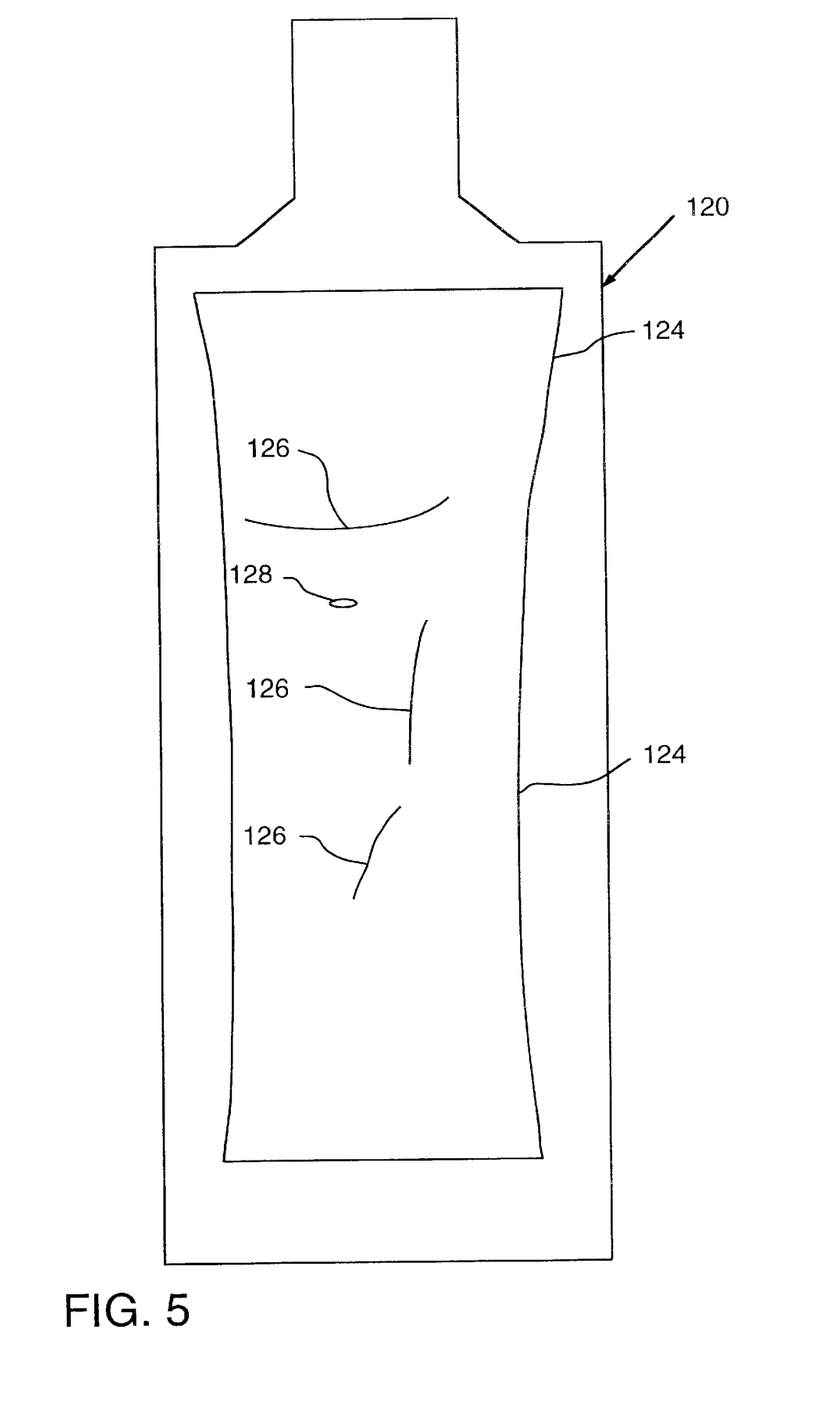
FIG. 5 shows an image of a bottle with examples of specific defects.

Referring to FIG. 5, there is shown a glass container 120 in cross-section. It has a number of desired variations, such as a general container slope changes 124, which is a purposeful variation, and refractive defects presented for purposes of illustration. The system and method of the present invention is designed to detect the presence of the lap marks 126 and the inclusion 128 while not causing the gentle container wall slope change 124 to appear as a refractive defect.

Figure 6:
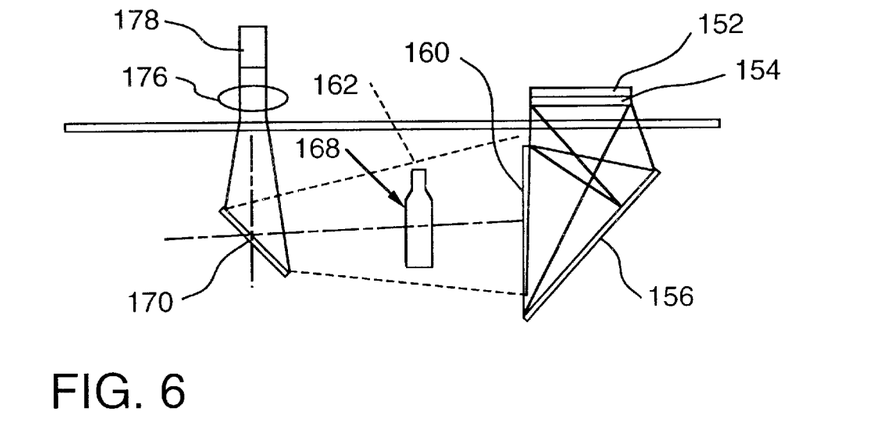
FIG. 6 is a schematic illustration of a modified form of the invention.

Referring to FIG. 6, a further embodiment of the present invention, which employs the same general concepts, but in a more compact configuration so as to minimize the space required for the apparatus, will be considered. In this embodiment, a light panel 152 has an associated grid filter 154 with a mirror 156 reflecting the light beams through the focusing lens 160 to cause the converging light beam 162 to impinge on container 168. A second mirror 170 causes the light beam to pass through lens 176 into detector 178.

Figures 7A, 7B:
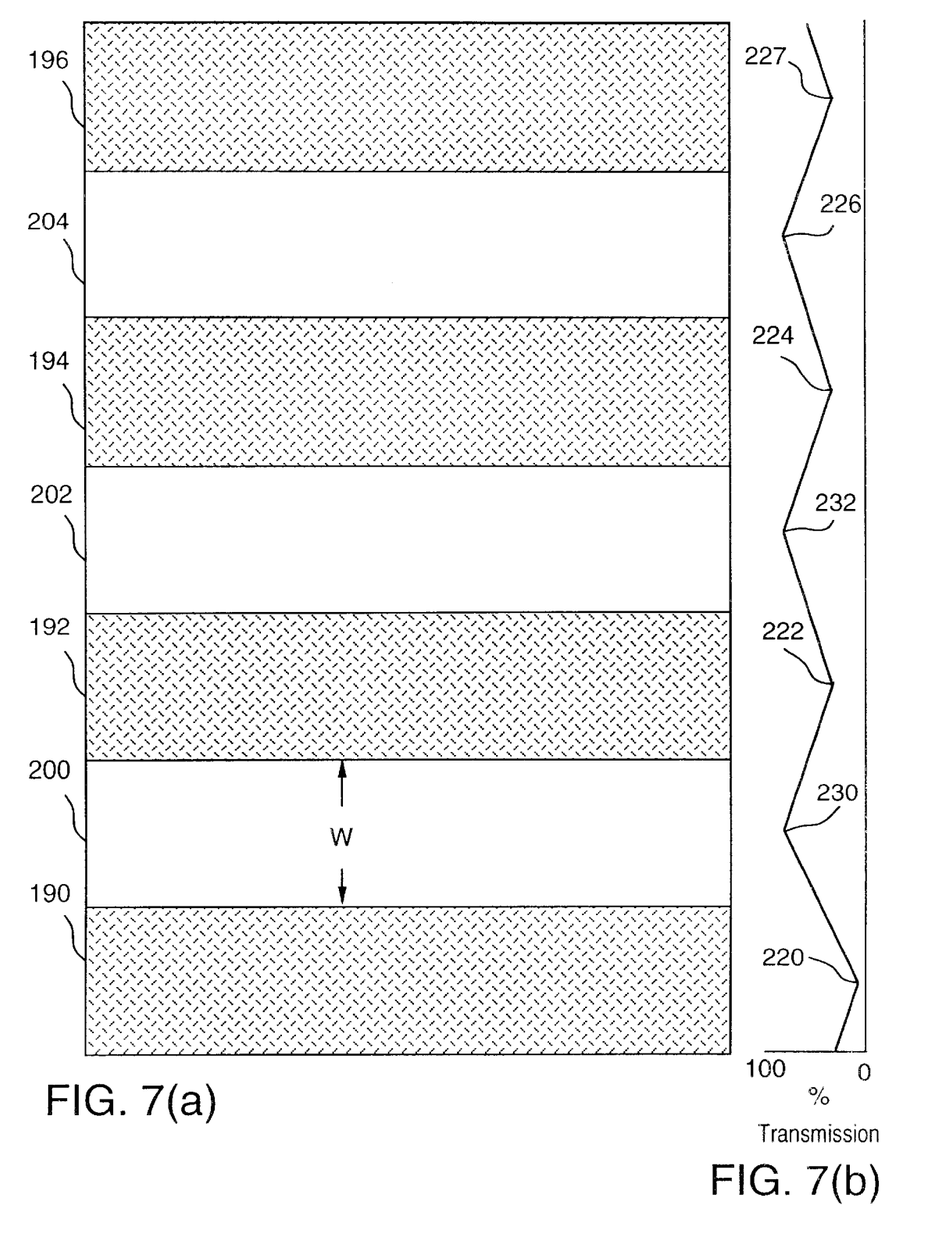
FIG. 7(a) is an image of a combination of a grid filter and vignetting mask and FIG. 7(b) is a plot of light intensity transmitted therethrough.

Referring to FIGS. 1, 7(a), and 7(b), the diffuser of the light source 2 is not a perfect Lambertian diffuser, and as a result, the light radiating from the optical axis B tends to be more intense at the center. In order to compensate for this, a vignette filter may be superimposed on the grid filter 4 in order to compensate for this variation. Such a filter provides alternating dark bands 190, 192, 194, 196 and light bands 200, 202, 204. It is preferred that the light bands 200, 202, 204 have a width W which is generally equal to the width of the dark bands 190, 192, 194, 196. In this embodiment, it will be noted that the minimum transmission appears at points 220, 222, 224 and 227 which are generally midway in the dark bands 190, 192, 194, 196 respectively, and the maximum light transmission 230, 232, 226 appears generally midway in the light bands 200, 202, 204. This serves to compensate for the greater intensity of light toward the center of grid filter 4. The vignette filter may be digitally combined with the grid filter into one filter.

Figure 8:
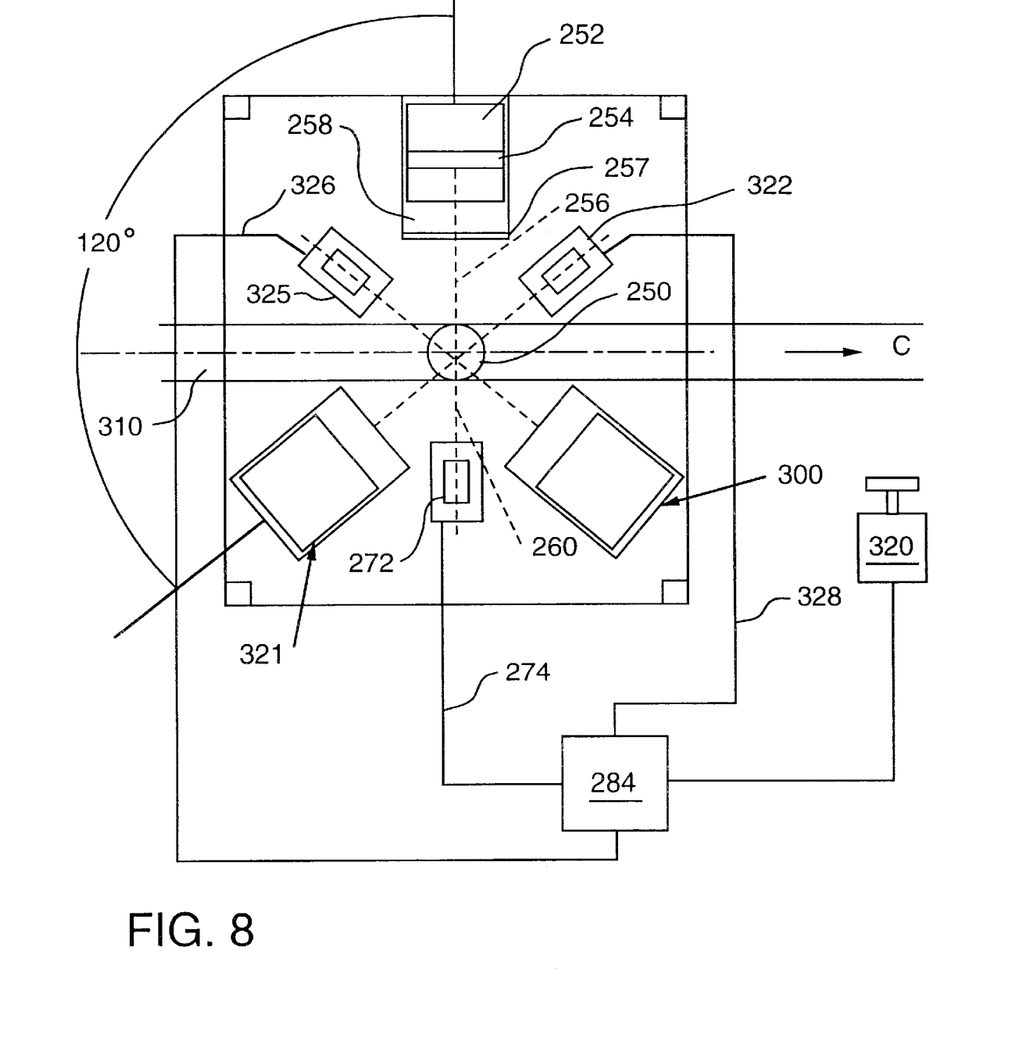
FIG. 8 is a plan schematic view showing an embodiment of the invention employing multiple inspection units inspecting overlapping regions of the circumference of the container being inspected.

Referring to FIG. 8, the use of multiple inspection systems of the present invention to permit simultaneous inspection of the full circumference of the container will be considered.

In this embodiment of the invention, a container 250 is positioned to be inspected by three inspection units of the present invention which are relatively spaced about 120° from each other. The systems may each be the form shown in FIG. 6 and employ mirrors to minimize the space occupied by each system. The light source 252 and grid filter 254 emit a gradient light beam 256. The emerging light beam enters detector 272 and by lead 274 delivers a corresponding electrical to processor 284. A focusing lens 257 focuses the light beam 256 on container 250. Similarly, system 300 and system 321 will have the same components and cause their light beams to impinge about 120° out of phase with respect to the adjacent two systems. Each system will inspect about 80° to 90° of the front wall and about 80° to 90° of the rear wall of the container at each side and will, therefore, cover 360° with 20° to 30° overlap in each view. Assuming that the container is moving in the direction shown by arrow C on conveyor 310, round container 250 may be effectively inspected for refractive defects.

If it is desired to inspect non-round containers, including rectangular containers, one inspection unit can be mounted perpendicular to the conveyor 310 such as the unit having light source 252 and the other two units will inspect each end respectively of the container. A suitable reject mechanism 320 which is adapted to mechanically remove any defective container from conveyor 310 is illustrated. In order to minimize undesired reflections from one unit's light into another detector camera, each unit may be spaced a small distance on the order of one inch farther down the line than the previous one. This allows for three sequential flashes before the next container enters the inspection area.

In the multiple detection mode, if any one unit detects a defect, the container is removed from the line. Detector units 325, 322 are connected respectively by leads 326, 328 to processor 284.

It will be appreciated that the present invention provides an efficient automated reliable means for detecting both structural and cosmetic refractive defects in transparent containers with greater sensitivity thereby permitting rejection of containers that might be objectionable from a cosmetic standpoint even though they are structurally sound. For example, containers for perfume and other high end products are such that it is desirable to avoid even relatively small cosmetic defects. The present system permits effective inspection for such subtle defects while resisting undesired rejection of containers having purposeful variations.

While for purposes of illustration herein, reference has been made generally to transparent containers, it will be appreciated that the invention is suitable for a wide variety of such containers, including but not limited to glass bottles and jars. The invention may also be employed with containers tinted with colors that adequately permit light transmission therethrough, such as amber, green, and blue containers, for example. Such containers shall be deemed to be "transparent" for purposes of the present invention.

Whereas particular embodiments of the invention have been described herein for purposes of illustration it will be evident to those skilled in the art that numerous variations of the details may be made without departing from the invention as set forth in the amended claims.

What is claimed is:

1. A method of inspecting a transparent container for refractive defects comprising
    providing a light source in spaced relationship with respect to a detector which is operatively associated with a processor for receiving electrical signals from said detector,
    providing a grid filter having a plurality of alternating dark and light bands,
    positioning said container between said light source and said detector with said grid filter positioned between said light source and said container,
    passing diffused light from said light source through said grid filter through said container to said detector to produce a generally triangular wave,
    converting said light received by said detector to corresponding electrical signals which are delivered to said processor, and
    determining by said processor employing said electrical signals whether a refractive defect exists in said container.
2. The method of claim 1 including
    performing said inspection without requiring axial rotation of said container.
3. The method of claim 2 including
    employing said inspection method on glass containers.
4. The method of claim 1 including
    employing a said grid filter having said bands generally horizontally oriented and of rectangular shape.
5. The method of claim 4 including
    employing a said grid filter having a generally sawtooth intensity profile.
6. The method of claim 5 including
    maintaining a substantially constant gradient over the field of view.
7. The method of claim 4 including
    directing the light passing through said grid filter onto said container by a lens.
8. The method of claim 1 including
    employing said grid with a band frequency of about 0.25 to 3 gradient bands per inch.
9. The method of claim 8 including
    employing as said grid filter dark bands having minimum transmission properties of about 0.1% to 5%, and said grid filter light bands having maximum transmission properties of about 70% to 10%.

10. The method of claim 9 including
said individual light bands having a width generally equal to the width of the individual dark bands.

11. The method of claim 9 including
said individual light bands having maximum light transmission generally midway between the edges thereof.

12. The method of claim 11 including
said individual dark bands having minimum light transmission characteristics generally midway between the edges thereof.

13. The method of claim 1 including
substantially simultaneously inspecting both the front and back surfaces of both the front and rear walls of said container.

14. The method of claim 1 including
providing a reject mechanism, and
causing said reject mechanism to remove a said container which is determined to have a said refractive defect.

15. The method of claim 1 including
employing as said detector a ccd camera.

16. The method of claim 1 including
effecting said inspection for refractive defects while ignoring desired irregularities in said container.

17. The method of claim 16 including
employing said processor to distinguish between objectionable refractive defects mad desired irregularities in said container.

18. The method of claim 1 including
employing a constant positive slope in the gradient between the darkest part of a said dark band and the lightest part of an adjacent said light band, and
employing a constant negative slope between the lightest part of a said light band and the darkest part of an adjacent said dark bank, whereby a constant gradient is established.

19. The method of claim 18 including
employing a said triangular wave having a constant absolute slope.

20. The method of claim 19 including
employing a vignette filter adjacent to said grid filter.

21. The method of claim 19 including
employing said processor to detect a said refractive defect by determining that the image of said triangular wave has been compressed by said defect to make the slope thereof steeper.

22. The method of claim 21 including
employing said dark bands with a minimum transmission rate of about 0.1% to 5%.

23. The method of claim 22 including
employing said light bands with a maximum transmission of about 70 to 100%.

24. The method of claim 18 including
making said process determination employing the absolute value of said slope.

25. The method of claim 1 including
simultaneously employing a plurality of inspection systems each including a said light source, a said grid filter, and a said detector.

26. The method of claim 25 including
each said circumferential portion being inspected by a said system overlapping adjacent said systems on opposite sides thereof.

27. The method of claim 25 including
said processor receiving electrical signals from each said detector.

28. The method of claim 1 including
employing said method to inspect an arc of about 80° to 90° about the circumference of said container.

29. The method of claim 1 including
said grid filter creating a sawtooth intensity profile.

30. Apparatus for inspecting transparent containers for refractive defects comprising
a light source for emitting diffuse light,
a grid filter having a plurality of alternating dark and light bands for converting said diffuse light into a multiple intensity light gradient having a generally triangular wave,
a container inspection station for supporting a container to be inspected and permitting said multiple intensity light gradient to pass through said container,
detecting means disposed on the opposite side of said container from said grid filter for receiving said filtered light as it passes through said container and emitting responsive electrical signals, and
a processor for receiving said electrical signals and determining if a said refractive defect exists in said container.

31. The apparatus of claim 30 including
said grid filter having said dark and light bands positioned in alternating relative relationship and being generally horizontally oriented.

32. The apparatus of claim 31 including
said dark bands and said light bands being of generally rectangular configuration.

33. The apparatus of claim 31 including
said grid bands having a zone frequency of about 0.25 to 3 gradient bands per inch.

34. The apparatus of claim 31 including
said individual light bands being of generally equal width to the width of said individual dark bands.

35. The apparatus of claim 31 including
said grid filter dark bands having minimum transmission properties of about 0.1% to 5%, and
said grid filter light bands having maximum transmission properties of about 70% to 100%.

36. The apparatus of claim 30 including
said processor containing means for distinguishing between refractive defects and purposeful irregularities in said container.

37. The apparatus of claim 30 including
reject means for removing a container responsive to receipt of a signal from said processor indicating that a refractive defect exists in said container.

38. The apparatus of claim 30 including
said individual light bands having maximum light penetration characteristics generally midway between the edges thereof.

39. The apparatus of claim 38 including
said individual dark bands having minimum light transmission characteristics generally midway between the adjacent edges thereof.

40. The apparatus of claim 30 including
a lens for directing said grid filtered light onto a said container.

41. The apparatus of claim 30 including said apparatus not having any means for effecting axial rotation of said container.

42. The apparatus of claim 30 including said apparatus being structured to inspect about 80° to 90° about the circumference of a said container.

43. The apparatus of claim 30 including said apparatus having means for simultaneously inspecting a plurality of overlapping arcs of said container wall.

44. The apparatus of claim 43 including said means for simultaneously inspecting a plurality of arcs including three said light sources, three said grid filters and three said detector means.

45. The apparatus of claim 30 including a vignette filter disposed adjacent said grid filter.

46. The apparatus of claim 45 including said grid filter and said vignette filter being digitally combined.

47. The apparatus of claim 30 including said grid filter being structured to create a sawtooth grid profile.

48. The apparatus of claim 30 including said grid filter structured to create a constant positive slope in the gradient between the darkest part of a said dark band and the lightest part of an adjacent said light band and a constant negative slope between the lightest part of a said light band and the darkest part of an adjacent said dark bank, whereby a constant gradient is established.

49. The apparatus of claim 30 including said grid filter structured to create a triangular wave having a constant absolute slope.

50. The apparatus of claim 49 including said processor being structured to detect a said refractive defect by determining that the image of said triangular wave has been compressed by said defect to make the slope thereof steeper.

51. The apparatus of claim 50 including said processor being structured to make said determination employing the absolute value of said slope.

* * * * *

UNITED STATES PATENT AND TRADEMARK OFFICE
CERTIFICATE OF CORRECTION

PATENT NO.     : 6,424,414 B1
DATED          : July 23, 2002
INVENTOR(S)    : Joseph G. Weiland et al.

It is certified that error appears in the above-identified patent and that said Letters Patent is hereby corrected as shown below:

Column 1,
Line 10, "provide:s" should read -- provides --.

Column 8,
Line 21, "amended" should read -- appended --.

Column 9,
Line 29, "mad" should read -- and --.
Line 38, "bank" should read -- band --.

Column 12,
Line 7, "bank" should read -- band --

Signed and Sealed this

Seventh Day of January, 2003

JAMES E. ROGAN
*Director of the United States Patent and Trademark Office*